United States Patent
Nakayama et al.

(10) Patent No.: US 9,441,194 B2
(45) Date of Patent: Sep. 13, 2016

(54) DEVICE FOR PRODUCING A THREE-DIMENSIONAL STRUCTURAL CELL

(75) Inventors: Koichi Nakayama, Saga (JP); Kenji Yoneda, Kanazawa (JP); Masahiro Sakamoto, Kanazawa (JP); Ichiro Koshida, Kanazawa (JP); Masaharu Shomura, Kanazawa (JP); Isao Fukamura, Kanazawa (JP)

(73) Assignees: NATIONAL UNIVERSITY CORPORATION SAGA UNIVERSITY, Saga, Saga (JP); CYFUSE BIOMEDICAL K.K., Tokyo (JP); SHIBUYA KOGYO CO., LTD., Kanazawa-shi, Ishikawa (JP)

( * ) Notice: Subject to any disclaimer, the term of this patent is extended or adjusted under 35 U.S.C. 154(b) by 189 days.

(21) Appl. No.: 14/126,681

(22) PCT Filed: Jun. 19, 2012

(86) PCT No.: PCT/JP2012/065568
§ 371 (c)(1),
(2), (4) Date: Dec. 16, 2013

(87) PCT Pub. No.: WO2012/176751
PCT Pub. Date: Dec. 27, 2012

(65) Prior Publication Data
US 2014/0120192 A1    May 1, 2014

(30) Foreign Application Priority Data

Jun. 24, 2011 (JP) .................... 2011-140111

(51) Int. Cl.
*C12M 1/26* (2006.01)
*C12M 3/00* (2006.01)
(Continued)

(52) U.S. Cl.
CPC ............. *C12M 33/04* (2013.01); *C12M 21/08* (2013.01); *C12M 23/12* (2013.01); *C12M 25/14* (2013.01); *C12M 25/16* (2013.01)

(58) Field of Classification Search
CPC ........................... C12M 23/12; C12M 33/04
See application file for complete search history.

(56) References Cited

U.S. PATENT DOCUMENTS

| 2005/0026221 A1* | 2/2005 | Richmond | ............. B01L 3/021 435/7.2 |
|---|---|---|---|
| 2008/0063572 A1* | 3/2008 | Deutsch | ............ B01L 3/502761 422/400 |

(Continued)

FOREIGN PATENT DOCUMENTS

| JP | 2006-141326 | 6/2006 |
|---|---|---|
| JP | 2006-271210 | 10/2006 |

(Continued)

OTHER PUBLICATIONS

English translation of International Search Report for PCT/JP2012/065568 (1 page).

*Primary Examiner* — Jill Warden
*Assistant Examiner* — Matthew Krcha
(74) *Attorney, Agent, or Firm* — Flynn, Thiel, Boutell & Tanis, P.C.

(57) ABSTRACT

A device 2 for producing a three-dimensional structural body has an accommodating plate 3 in which an accommodating recess portion 3a for accommodating a cell mass 1 is formed, a support body 4 provided with a plurality of needle-shaped bodies 6 penetrating the cell mass, a suction nozzle 19 for adsorbing/holding the cell mass, and structure 20 for moving the suction nozzle.

6 Claims, 4 Drawing Sheets

(51) Int. Cl.
*C12M 1/32* (2006.01)
*C12M 1/12* (2006.01)

(56) References Cited

U.S. PATENT DOCUMENTS

2008/0257074 A1* 10/2008 Fuchiwaki ............ C12M 33/04
73/864.14

2011/0200559 A1* 8/2011 Koga .................. A61L 27/3843
424/93.1

FOREIGN PATENT DOCUMENTS

| | | |
|---|---|---|
| JP | 4517125 | 5/2010 |
| WO | WO 2008/123614 A1 | 10/2008 |

* cited by examiner (a)　　　　　　(b)　　　　　　(c)

(a)　　　　　　(b)　　　　　　(c)

(a)   (b)   (c)

DEVICE FOR PRODUCING A THREE-DIMENSIONAL STRUCTURAL CELL

TECHNICAL FIELD

The present invention relates to a device for producing a three dimensional structural cell and more particularly to a device for producing a three-dimensional structural cell which produces a three-dimensional structural body by a plurality of cells by sticking a needle-shaped body provided on a support into a cell mass.

BACKGROUND ART

With the purpose of use for medical cell transplant for reproduction of organs or internal organs and for other tests, production of a three-dimensional structural body of cells has been practiced by combining a plurality of cell masses (spheroids) in a three-dimensional manner.

In order to produce such three-dimensional structural bodies of cells, use of a support body provided with a plurality of needle-shaped bodies is known, and the needle-shaped bodies are stuck into the plurality of cell masses so as to bring the cell masses close to each other, whereby the three-dimensional structural bodies of the cells are obtained.

In the conventional arts, in order to stick the needle-shaped body of the support body into the cell masses, a-manual work was performed by using a pipette having suctioned the cell masses, a robot arm, and tweezers (Patent Literature 1).

PRIOR ART DOCUMENTS

Patent Literature

Patent Literature 1: Japanese Patent No. 4517125

SUMMARY OF INVENTION

Problems to be Solved by the Invention

However, the cell masses have a diameter of approximately several hundreds μm, and there was a problem that the work to stick the needle-shaped body having a diameter of several tens μm into them was very difficult.

In view of the above problem, the present invention provides a device for producing a three-dimensional structural cell which can obtain the three-dimensional structural body of a cell by automatically sticking the needle-shaped body of the support body into the cell masses.

Means for Solving the Problems

That is, a device for producing a three-dimensional structural cell according to the present invention of claim (1) is provided with an accommodating plate in which a large number of accommodating recess portions, each accommodating one cell mass, are formed, a support body provided with a plurality of needle-shaped bodies sticking and penetrating the cell mass, a suction nozzle for adsorbing/holding the cell mass by being connected to negative pressure generating means, moving means for moving and elevating the suction nozzle between the accommodating plate and the support body, and control means for controlling a suctioning operation of the suction nozzle and an operation of the moving means, in which the suction nozzle is provided with a tubular adsorbing portion for adsorbing one cell mass at a tip end thereof, an inner diameter of the adsorbing portion is formed smaller than an outer diameter of the cell mass and larger than an outer peripheral diameter of the needle-shaped body of the support body;

the control means is configured such that, when the cell mass is adsorbed/held by the adsorbing portion of the suction nozzle in the accommodating recess portion of the accommodating plate, the suction nozzle is moved to above the required needle-shaped body in the support body by the moving means; and the suction nozzle is further moved in an axial direction of the needle-shaped body, the needle-shaped body is stuck into the cell mass, and the needle-shaped body penetrating the cell mass is inserted into the adsorbing portion.

Advantageous Effects of Invention

According to the above invention, since the suction nozzle is moved by the moving means so that the cell mass in the accommodating plate is adsorbed/held and is stuck by the needle-shaped body of the support body, production of a three-dimensional structural body by the cell mass can be performed automatically.

At that time, since the inner diameter of the adsorbing portion of the adsorption nozzle is formed smaller than the outer diameter of the cell mass and larger than the outer peripheral diameter of the needle-shaped body and the moving means moves the suction nozzle having adsorbed/held the cell mass in the axial direction of the needle-shaped body, the cell mass can be reliably stuck by the needle-shaped body.

BRIEF DESCRIPTION OF DRAWINGS

FIG. 2 is views illustrating an accommodating plate, in which FIG. 2(a) is a perspective view, FIG. 2(b) is an enlarged sectional view of an accommodating recess portion, and FIG. 2(c) is a plan view of the accommodating recess portion.

FIG. 3 is views illustrating a support body, in which FIG. 3(a) is a side view, FIG. 3(b) is a side view of a state in which a needle-shaped body sticks the cell mass, and FIG. 3(c) is a plan view of the support body.

MODE FOR CARRYING OUT THE INVENTION

Figure 1:
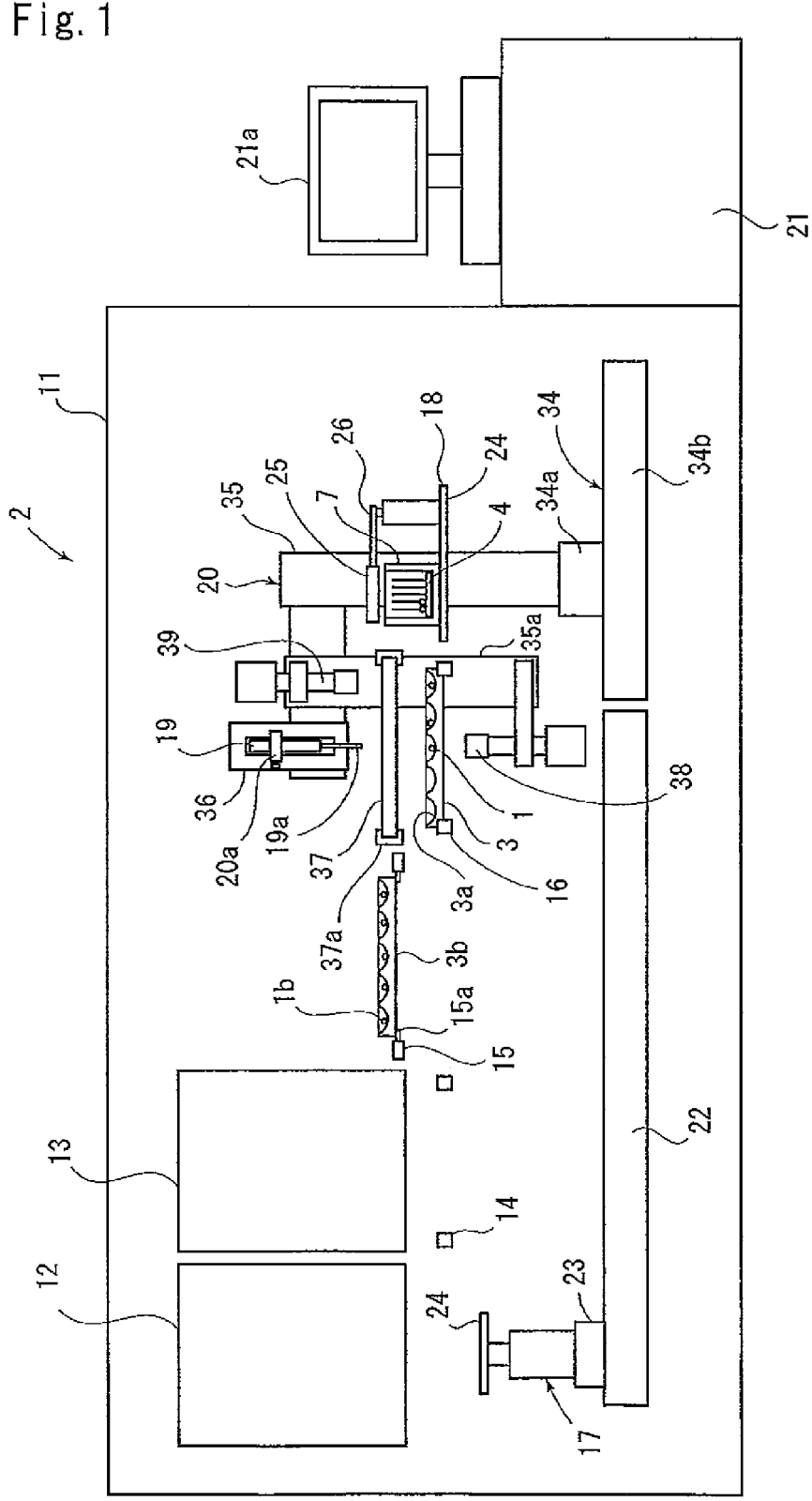
FIG. 1 is a configuration diagram of a device for producing a three-dimensional structural cell according to a present embodiment.

An illustrated embodiment will be described below, in which FIG. 1 illustrates a device 2 for producing a three-dimensional structural body for producing a three-dimensional structural cell by combining a plurality of cell masses 1 (spheroids) in a three-dimensional manner.

Figure 2:
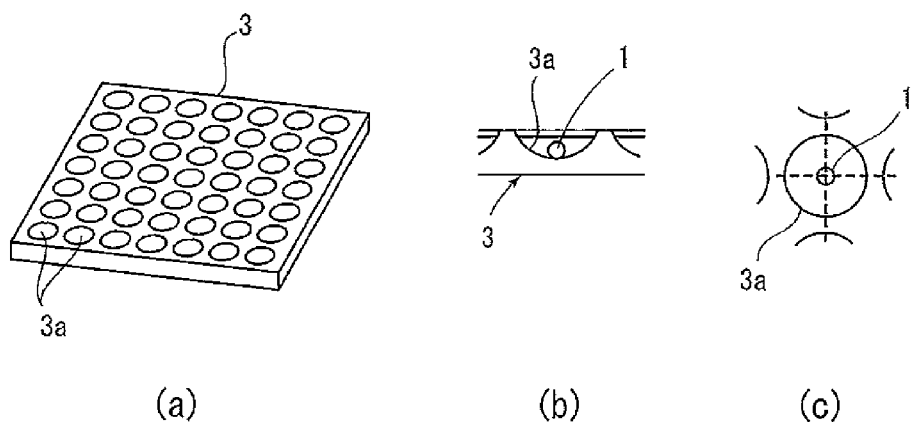
Figure 3:
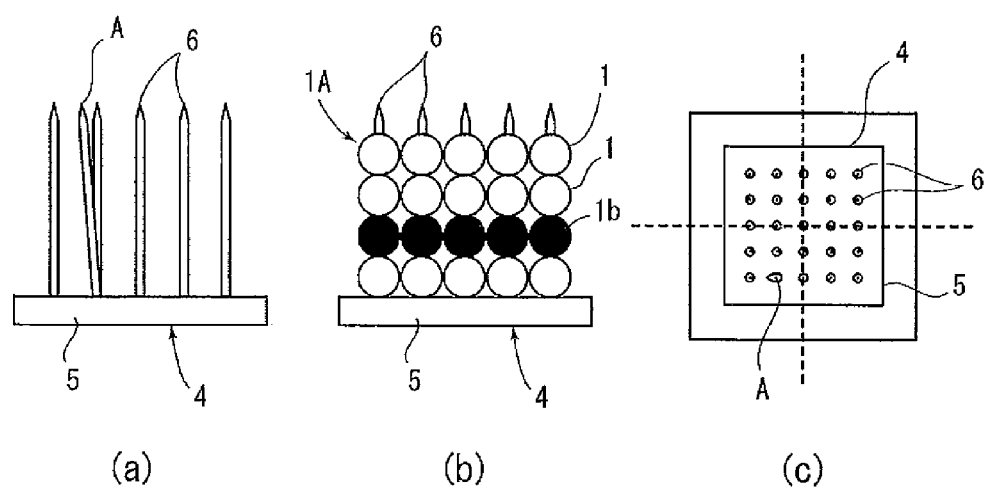

In this device 2 for producing a three-dimensional structural body, by using a suction nozzle 19 which will be described later in detail, a cell mass 1 is taken out of an accommodating plate 3 illustrated in FIG. 2 one by one and the cell mass 1 is stuck one by one by a needle-shaped body 6 of a support body 4 illustrated in FIG. 3(*a*) so that a three-dimensional structural body 1A of a cell as illustrated in FIG. 3(*b*) is produced. The accommodating plate 3 is produced of a transparent member, and a plurality of accommodating recess portions 3*a* are formed laterally and longitudinally. Each of the accommodating recess portions 3*a* illustrated in FIG. 2(*b*) is constituted by a recess portion with a spherical bottom surface, and each of the accommodating recess portions 3*a* accommodates a culture fluid and one substantially spherical cell mass 1 thereinside.

Moreover, in the present embodiment, it is possible to produce the three-dimensional structural body 1A by mixing partially different kinds of different-kind cell masses 1*b*, and thus, the accommodating plate 3 accommodating the cell mass 1 and a different-kind accommodating plate 3*b* for accommodating the different-kind cell mass 1*b* can be prepared.

The support body 4 is composed of a substantially regular square plate-shaped member 5 and a plurality of the needle-shaped bodies 6 installed upright on a surface of the plate-shaped member 5, and in the present embodiment, the needle-shaped bodies 6 are provided in the number of 5 pieces in a vertical direction and 5 pieces in a lateral direction, totaling 4-25 pieces, on the surface of the plate-shaped member 5. The number of the needle-shaped bodies 6 is not limited to this.

This support body 4 is accommodated in an accommodating vessel 7 illustrated in FIG. 1, when it is used in the device 2 for producing a three-dimensional structural body and this accommodating vessel 7 is a bottomed vessel with an upper part open and is positioned by being fitted with the plate-shaped member 5 when it accommodates the support body 4.

The needle-shaped body 6 is made of metal and has a length with which it can stick a plurality of (4 pieces in this embodiment) cell masses 1, respectively, and an interval between the adjacent needle-shaped bodies 6 is set at such an interval that the stuck cell masses 1 are brought into close contact with each other, that is, an interval of approximately one cell mass 1.

By sticking each of the needle-shaped bodies 6 into the plurality of cell masses 1 and by stacking the cell masses 1 from a root side to a tip end side of the needle-shaped body 6, the three-dimensional structural body 1A of a cell as illustrated in FIG. 3(*b*) is obtained. At this time, by combining a different-kind cell mass 1*b* as appropriate, the three-dimensional structural body 1A of a cell in which the different-kind cell masses 1*b* are mixed can be obtained.

Though the needle-shaped body 6 is installed substantially perpendicularly to the plate-shaped member 5, the largely inclined needle-shaped body 6 indicated by A in FIG. 3(*a*) is included depending on need.

The device 2 for producing a three-dimensional structural body is provided with a clean bench 11 having an inside kept in an aseptic state, a supply magazine 12 for accommodating an accommodating plate 3 which has accommodated the cell mass 1, a recovery magazine 13 for recovering the accommodating plate 3 from which the cell mass 1 has been taken out, first support means 14 for supporting the accommodating plate 3 arranged below the recovery magazine 13, second support means 15 for supporting a different-kind accommodating plate 3*b* accommodating the different-kind cell mass 1*b*, third support means 16 arranged adjacently to the support body 4 and supporting the accommodating plate 3 and the different-kind accommodating plate 3*b*, transfer means 17 for transferring the accommodating plate 3 and the different-kind accommodating plate 3*b*, a placing base 18 on which the accommodating vessel 7 accommodating the support body 4 is placed, a suction nozzle 19 for adsorbing/holding the cell mass 1, and moving means 20 for moving and elevating the suction nozzle 19.

The device 2 for producing a three-dimensional structural body having the aforementioned configuration is controlled by control means 21 provided adjacently to the clean bench 11, and this control means 21 is capable of various settings by a terminal such as a personal computer 21*a* or the like.

The clean bench 11 is capable of being opened/closed by an opening/closing door, not shown, and of carrying' in/out the supply magazine 12, the recovery magazine 13, and the accommodating vessel 7 accommodating the support body 4.

On an upper part of the clean bench 11, aseptic air supply means, not shown, for supplying an aseptic air is provided so that, in a state in which the opening/closing door is closed, a one-way flow of the aseptic air from an upper side to a lower side is formed inside the clean bench 11.

The supply magazine 12 and the recovery magazine 13 are capable of holding the plurality of accommodating plates 3 in a stacked state, respectively, and the second support means 15 is provided at a position adjacent to a side of the recovery magazine 13.

The first and third support means 14 and 16 are arranged at the same height and constituted by four support members supporting four corners of the accommodating plate 3 from below, and the transfer means 17 is configured to place the accommodating plate 3 from above on the first and third support means 14 and 16.

On the other hand, the second support means 15 is provided slightly above the first and third support means 14 and 16 and is provided with an engaging claw 15*a* capable of advancing/retracting for supporting the four corners of the different-kind accommodating plate 3*b* from below.

The second support means 15 is configured to support the different-kind accommodating plate 3*b* from below by protrusion of the engaging claw 15*a*, and when the different-kind accommodating plate 3*b* is transferred from the second support means 15 to the transfer means 17 or when the different-kind accommodating plate 3*b* is transferred from the transfer means 17 to the second support means 15, the engaging claw 15*a* is retracted so as to allow vertical movement of the different-kind accommodating plate 3*b*.

The transfer means 17 is composed of a slide mechanism 22 provided linearly below the supply magazine 12, the recovery magazine 13, and the first to third support means 14 to 16 and an elevating table 24 provided on a movable portion 23 of the slide mechanism 22.

The elevating table 24 lowers when the first to third support means 14 to 16 support the accommodating plate 3 or the different-kind accommodating plate 3*b* and is located above the first and third support means 14 and 16 and below the second support means 15 when the accommodating plate 3 or the different-kind accommodating plate 3*b* are transferred and moves the accommodating plate 3 or the different-kind accommodating plate 3*b* by an operation of the slide mechanism 22 in that state.

On the placing base 18, the accommodating vessel 7 for accommodating the support body 4 is positioned and placed, and a ring illumination 25 for illuminating the accommodating vessel 7 is provided through turning means 26 for turning/moving the ring illumination 25 so that the ring illumination 25 is turned/moved between above the accommodating vessel 7 and a position retreated therefrom.

Figure 4:
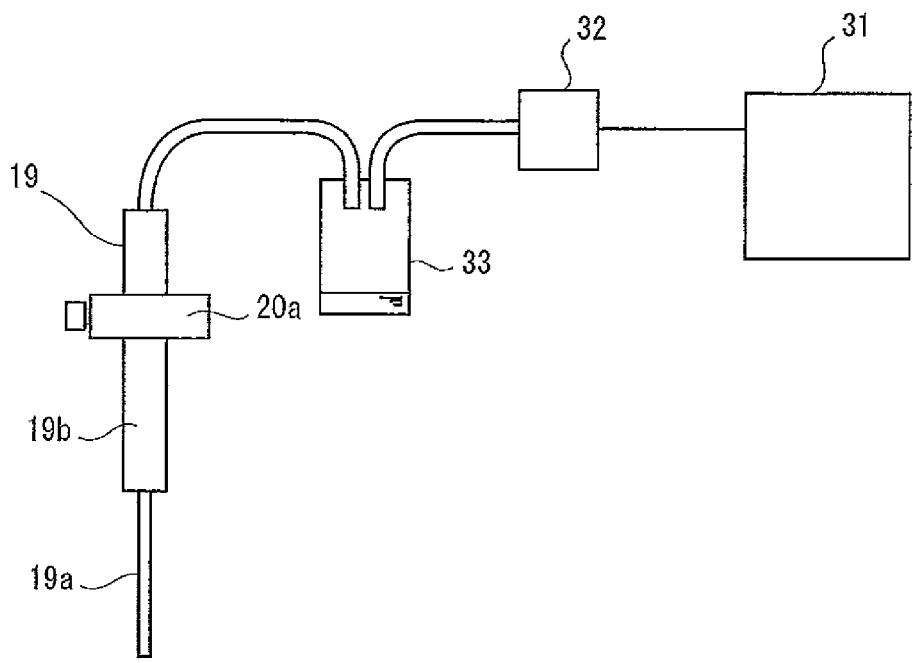
FIG. 4 illustrates a configuration diagram of a suction nozzle.

As illustrated in FIG. 4, the suction nozzle 19 is connected to negative-pressure generating means 31 for generating a negative pressure, a regulator 32 for regulating the negative pressure generated by the negative-pressure generating means 31, and a buffer vessel 33 reserving a culture fluid suctioned by the suction nozzle 19 with adsorption of the cell mass 1 via a piping.

The suction nozzle 19 is provided with a tubular adsorbing portion 19a for adsorbing one cell mass at its tip end and a body portion 19b held by the moving means 20 and is attached to the moving means 20 by fixing means 20a, capable of replacement.

Figure 5:
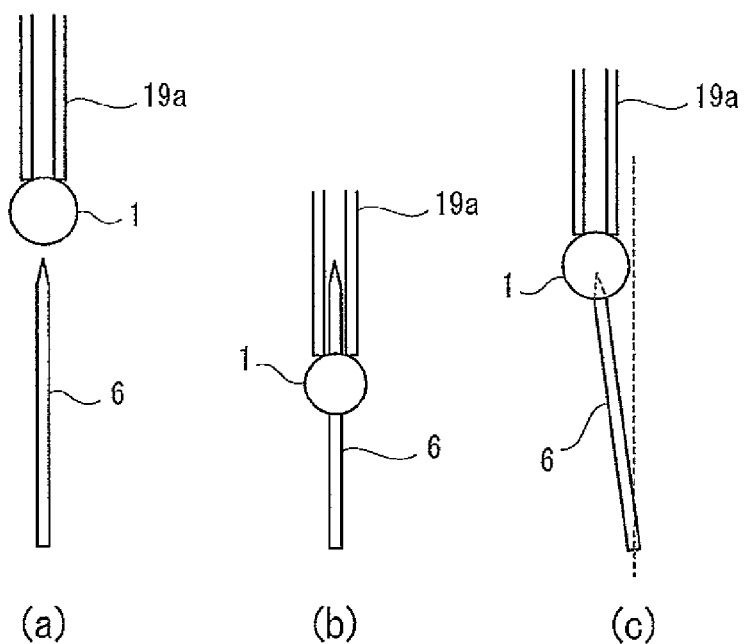
FIG. 5 is diagrams for explaining a process of sticking the cell mass by the needle-shaped body by using the suction nozzle.

The adsorbing portion 19a has its inner diameter smaller than an outer diameter of the cell mass 1 and larger than an outer peripheral diameter of the needle-shaped body 6 of the support body 4. By setting such dimensions, as illustrated in FIG. 5(a), the one cell mass 1 can be adsorbed at the tip end, and moreover, as illustrated in FIG. 5(b), the needle-shaped body 6 penetrating the cell mass 1 can be inserted into the adsorbing portion 19a so as to push in the cell mass 1.

The moving means 20 is composed of an X-Y unit 34 as a horizontal moving mechanism provided at a position adjacent to the transfer means 17 as illustrated in FIG. 1, a movable support portion 35 moving horizontally by the X-Y unit 34, and elevating means 36 provided on an upper part of the movable support portion 35 and elevating the suction nozzle 19.

The X-Y unit 34 is composed of a Y-direction mechanism 34a for moving the movable support portion 35 in a direction orthogonal to a transfer direction of the transfer means 17 and an X-direction mechanism 34b for moving the Y-direction mechanism 34a in a direction orthogonal to the moving direction.

On a movable portion of the elevating means 36, the suction nozzle 19 is fixed through the fixing means 20a, and by moving the movable support portion 35 in a horizontal direction by the X-Y unit 34, the suction nozzle 19 can be moved between the accommodating plate 3 or the different-kind accommodating plate 3a supported by the third support means 16 and the accommodating vessel 7 placed on the placing base 18, and also by vertically elevating the suction nozzle 19 by the elevating means 36, the cell mass 1 or different-kind cell mass 1b in the accommodating recess portion 3a of the accommodating plate 3 or the different-kind accommodating plate 3b can be adsorbed or held, or the held cell mass 1 or different-kind cell mass 1b can be stuck by the needle-shaped body 6 of the support body 4.

Above the third support means 16, a panel illumination 37 is provided and performs plane light emitting with substantially the same area as that of the accommodating plate 3 or the different-kind accommodating plate 3b supported by the third support means 16 and emits light onto the entirety of the accommodating plate 3 or the different-kind accommodating plate 3b.

Moreover, the panel illumination 37 is reciprocally moved by a slide mechanism 37a from above the third support means 16 to a side in the transfer direction of the transfer means 17 and is capable of retreating so as not to interfere with the lowering of the suction nozzle 19 to the accommodating plate 3 or the different-kind accommodating plate 3b supported by the third support means 16.

On the upper part of the movable support portion 35, a mounting member 35a which is long downward is provided side by side with the elevating means 36, and a lower camera 38 is mounted on a lower part of the mounting member 35a, and an upper camera 39 on the upper part, respectively.

The lower camera 38 is arranged so as to be located immediately below the suction nozzle 19, and the accommodating plate 3 or the different-kind accommodating plate 3b supported by the third support means 16 and the panel illumination 37 are located between the lower camera 38 and the suction nozzle 19.

The lower camera 38 photographs the transparent accommodating plate 3 or different-kind accommodating plate 3b from below. Its photographing range is, as illustrated in FIG. 2(c), set to a range capable of photographing one accommodating recess portion 3a, and a center of a visual field is an intersection between two center lines illustrated in FIG. 2(c).

An image photographed by the lower camera 38 is transmitted to the control means 21, and the control means 21 recognizes the position in the accommodating recess portion 3a of the cell mass 1 accommodated in this accommodating recess portion 3a and also recognizes an outer diameter and a shape of the cell mass 1.

Figure 6:
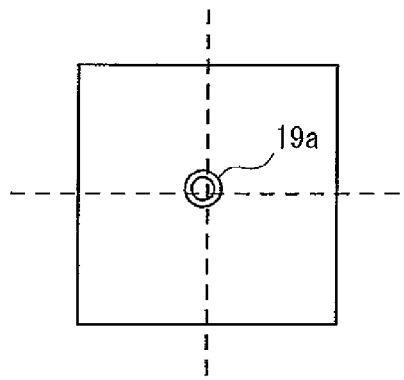
FIG. 6 is a diagram of the suction nozzle taken by a camera below.

Moreover, in a state in which the accommodating plate 3 or the panel illumination 37 is not located between them, the tip end of the adsorbing portion 19a attached to the suction nozzle 19 as illustrated in FIG. 6 can be photographed from below.

The upper camera 39 is located above the support body 4 accommodated in the accommodating vessel 7 positioned on the placing base 18 by an operation of the X-Y unit 34 of the moving means 20 and is configured to photograph all the needle-shaped bodies 6 as illustrated in FIG. 3(c).

An image photographed by the upper camera 39 is transmitted to the control means 21, and the control means 21 recognizes a tip-end position of the needle-shaped body 6 provided on this support body 4.

An operation of the device 2 for producing a three-dimensional structural body having the aforementioned configuration will be described below.

First, a worker sets the supply magazine 12 accommodating the accommodating plate 3 accommodating the cell mass 1 and the empty recovery magazine 13 and also places the different-kind accommodating plate 3b accommodating the different-kind cell mass 1b on the second support means 15. Moreover, the worker positions the accommodating vessel 7 accommodating the support body 4 on the placing base 18 and attaches the new adsorbing portion 19a to the suction nozzle 19.

Moreover, by using the personal computer 21a connected to the control means 21 in advance, a structure of the three-dimensional structural body 1A of a cell to be produced is set, and arrangement of the cell mass 1 and the different-kind cell mass 1b is set as illustrated in FIG. 3(b).

First, the control means 21 measures a position of the tip end of the adsorbing portion 19a of the attached suction nozzle 19. Specifically, in a state in which the panel illumination 37 is retracted, the adsorbing portion 19a of the suction nozzle 19 is photographed by the lower camera 38, and an image illustrated in FIG. 6 is obtained.

The control means 21 measures how much a center of the adsorbing portion 19a is shifted with respect to the center of the visual field of the lower camera 38 through image processing and stores the shift amount. This shift amount is added when the suction nozzle 19 is positioned at positions of the cell mass 1 or the different-kind cell mass 1b and the needle-shaped body 6 by the operation of the X-Y unit 34 of the moving means 20.

Subsequently, the elevating table 24 of the transfer means 17 is elevated, the single accommodating plate 3 is taken out of the supply magazine 12, and the accommodating plate 3 is transferred to the third support means 16 as it is.

When the accommodating plate 3 is supported by the third support means 16 as above, the panel illumination 37 is moved to above the accommodating plate 3, the suction nozzle 19 and the lower camera 38 are moved in the horizontal direction by the operation of the X-Y unit 34 of the moving means 20, and they are located above and below the accommodating recess portion 3a accommodating the cell mass 1 to be taken out.

At this time, the X-Y unit 34 moves the lower camera 38 in accordance with the position of each of the accommodating recess portions 3a of the accommodating plate 3 stored in advance and positions the entire accommodating recess portion 3a within the visual field of the lower camera 38.

When the lower camera 38 is to photograph the accommodating recess portion 3a, the panel illumination 37 emits light from above the accommodating plate 3 and can clearly recognize the accommodated cell mass 1 from below the transparent accommodating plate 3, and the control means 21 recognizes the position of the photographed cell mass 1 in the accommodating recess portion 3a and measures the size (outer diameter dimension) and the shape.

Figure 7:
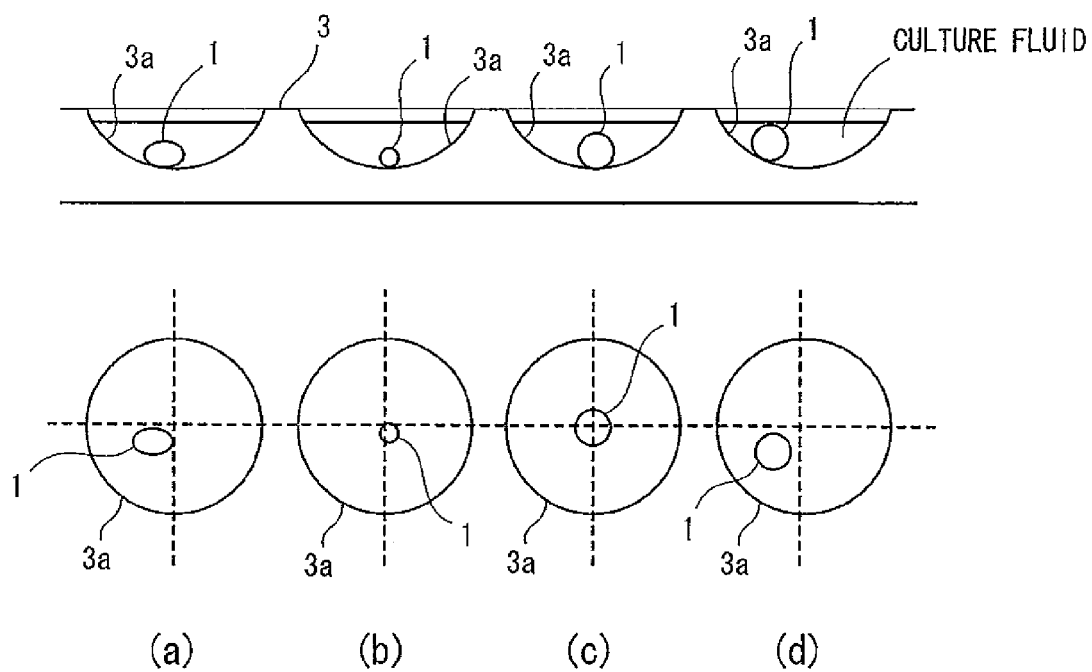
FIG. 7 is diagrams illustrating the cell mass accommodated in the accommodating recess portion.

Each of FIG. 7 illustrates a photographed result of the cell mass 1 photographed by the lower camera 38, in which the cell mass 1 illustrated in FIG. 7(a) does not have a proper shape, and the cell mass 1 illustrated in FIG. 7(b) has the outer-diameter dimension short of a predetermined size.

The control means 21 determines that such cell masses 1 are not to be used for the three-dimensional structural body 1A of a cell and does not perform an adsorbing/holding operation by the suction nozzle 19.

On the other hand, FIGS. 7(c) and 7(d) illustrate the cell masses 1 having appropriate shapes and outer-diameter dimensions, but, in FIG. 7(c), the cell mass 1 is located at the center of the accommodating recess portion 3a, and in FIG. 7(d), the cell mass 1 is shifted from the center of the accommodating recess portion 3a.

Since the bottom surface of the accommodating recess portion 3a of the accommodating plate 3 has a semispherical shape, if the cell mass 1 is located at the center as in FIG. 7(c), the cell mass 1 is located at the deepest position in the accommodating recess portion 3a, and if it is shifted from the center as in FIG. 7(d), the cell mass 1 is located at a position shallower than the deepest position in the accommodating recess portion 3a.

The control means 21 grasps a depth corresponding to a position on the bottom surface of the accommodating recess portion 3a. Moreover, since the cell mass 1 has a substantially spherical shape, its height can be estimated from the outer-diameter dimension (diameter). The control means 21 sets a lowering amount of the suction nozzle 19 when the cell mass 1 is adsorbed/held, by recognizing the position in the accommodating recess portion 3a and by measuring the outer-diameter dimension of the cell mass 1.

After the cell mass 1 in the accommodating portion 3a is photographed by the lower camera 38 as above, the control means 21 retracts the panel illumination 37 from above the accommodating plate 3, moves the suction nozzle 19 in the horizontal XY direction by operating the X-Y unit 34 of the moving means 20, and positions it to a position of the recognized cell mass 1 and moreover, lowers the suction nozzle 19 by the elevating means 36 in accordance with the set lowering amount and brings the adsorbing portion 19a closer to the cell mass 1 so as to have the adsorbing portion 19a absorb the cell mass 1.

Since the outer diameter of the cell mass 1 is larger than the inner diameter of the adsorbing portion 19a, the cell mass 1 can be adsorbed/held at the tip end without being suctioned into the adsorbing portion 19a.

After the cell mass 1 is adsorbed/held by the suction nozzle 19 as above, the suction nozzle 19 is raised by the elevating means 36, and the panel illumination 37 is located above the accommodating plate 3 again.

The lower camera 38 photographs the accommodating recess portion 3a this time again and confirms that the cell mass 1 has been removed. If the cell mass 1 remains, a process of adsorbing/holding the cell mass 1 by the suction nozzle 19 is retried again.

When the suction nozzle 19 adsorbs and holds the cell mass 1 as above, the control means 21 operates the X-Y unit 34 of the moving means 20 so as to move the upper camera 39 to above the support body 4 and recognizes the tip end position of the needle-shaped body 6 for sticking the cell mass 1 this time.

At this time, the ring illumination 25 is located above the accommodating vessel 7 and illuminates the support body 4 and when the tip end position of the needle-shaped body 6 is recognized by the upper camera 39, the ring illumination 25 is retreated by the turning means 26.

If the tip end position of the needle-shaped body 6 is recognized, the control means 21 operates the X-Y unit 34 so as to move the adsorbing portion 19a of the suction nozzle 19 adsorbing/holding the cell mass 1 to above the tip end position of the needle-shaped body 6 recognized as above on the support body 4 and moreover, lowers the suction nozzle 19 so as to stick the cell mass 1 by the tip end of the needle-shaped body 6 as illustrated in FIG. 5(a).

From this state, when the elevating means 36 moves the suction nozzle 19 downward as illustrated in FIG. 5(b), the cell mass 1 pressed by the adsorbing portion 19a from above is penetrated by the needle-shaped body 6, and the needle-shaped body 6 is inserted into the adsorbing portion 19a.

Moreover, the lowering amount of the suction nozzle 19 is set in advance but is configured to be modified on the basis of the outer diameter dimension of the cell mass 1 previously recognized by the lower camera 38.

Here, the inner diameter of the adsorbing portion 19a of the adsorption nozzle 19 in this embodiment is set smaller than the cell mass 1 and larger than the outer peripheral diameter (thickness) of the needle-shaped body 6, and the moving means 20 moves the suction nozzle 19 adsorbing/holding the cell mass 1 in an axial direction of the needle-shaped body 6, and thus, the cell mass 1 can be reliably stuck by the needle-shaped body 6.

On the other hand, as the result of recognition of the tip end position of the needle-shaped body 6, if the tip end position of the needle-shaped body 6 to stick the cell mass 1 is out of the specified range, the control means 21 has the cell mass 1 stuck at the tip end position of the needle-shaped body 6 out of the range as illustrated in FIG. 5(c) and then, moves the suction nozzle 19 in the horizontal direction so as to move the tip end position to within the specified range, whereby an attitude of the needle-shaped body 6 is corrected, and then, lowers the suction nozzle 19.

An operation when the different-kind cell mass 1b is transferred onto the support body 4 will be described below.

In this case, the control means 21 controls the transfer means 17 so as to transfer the accommodating plate 3 supported by the third support means 16 to the first support means 14 and moreover, the transfer means 17 places the different-kind accommodating plate 3b supported by the second support means 15 onto the elevating table 24.

In that state, the engaging claw 15a of the second support means 15 is retracted, the elevating table 24 is lowered, and the accommodating plate 3b is transferred to the third support means 16. In this state, similarly to the case of the cell mass 1 accommodated in the accommodating plate 3, the different-kind cell mass 1b accommodated in the accommodating recess portion 3a of the different-kind accommodating plate 3b is processed.

Moreover, if the cell masses 1 are taken out of all the accommodating recess portions 3a in the accommodating plate 3, the transfer means 17 transfers the empty accommodating plate 3 supported by the third support means 16 to below the recovery magazine 13 and accommodates it in the recovery magazine 13.

REFERENCE SIGNS LIST 1 cell mass
1A three-dimensional structural body of cell
1b different-kind cell mass
2 device for producing three-dimensional structural body
3 accommodating plate
3a accommodating recess portion
4 support body
6 needle-shaped body
19 suction nozzle
19a adsorbing portion
20 moving means
21 control means
38 lower camera (cell mass photographing means)
39 upper camera (needle-shaped body photographing means)

The invention claimed is:

1. A device for producing a three-dimensional structural cell, comprising:
    an accommodating plate comprising an accommodating recess portion formed therein and containing one cell mass;
    a support body provided with a plurality of needle-shaped members;
    a suction nozzle having a tubular adsorbing portion for adsorbing/holding one cell mass at a tip end thereof;
    a moving mechanism for moving and elevating the suction nozzle;
    a lower camera for photographing the cell mass accommodated in the accommodating recess portion of the accommodating plate; and
    a controller configured to measure the outer diameter dimension of the cell mass in the accommodating recess portion photographed by the lower camera to determine whether or not to adsorb and hold a cell mass having an outer diameter that does not reach a predetermined outer diameter dimension larger than the inner diameter of the tubular adsorbing portion, control the moving mechanism to lower the suction nozzle so that the cell mass is adsorbed and held by the tubular adsorbing portion and to move the suction nozzle above a specified needle-shaped member on the support body for a cell mass having an outer diameter that reaches the predetermined outer diameter dimension, and move the suction nozzle in an axial direction of the needle-shaped member to stick and penetrate the cell mass by the needle-shaped member and insert the needle-shaped member into the adsorbing portion so as to push in the cell mass.

2. The device for producing a three-dimensional structural cell according to claim 1, wherein intervals between adjacent needle-shaped members in the support body are such that cell masses stuck by the respective needle-shaped member are brought into close contact with each other.

3. The device for producing a three-dimensional structural cell according to claim 1, wherein the lower camera is positioned below the suction nozzle for photographing the suction nozzle, an upper camera is positioned above the support body for photographing the needle-shaped members and the controller is configured to control the moving mechanism on the basis of the position of the adsorbing portion of the suction nozzle photographed by the lower camera and the tip end position of the specified needle-shaped member photographed by the upper camera and move the suction nozzle adsorbing/holding the cell mass to above the specified needle-shaped member.

4. The device for producing a three-dimensional structural cell according to claim 3, wherein the controller is configured to move the suction nozzle when a cell mass adsorbed/held by the suction nozzle is stuck by the tip end of the needle-shaped member and the tip end of the needle-shaped member photographed by the upper camera is not located within a specified range to a position such that the tip end of the needle-shaped member is located within the specified range.

5. The device for producing a three-dimensional structural cell according to claim 3, wherein the accommodating plate is transparent and the lower camera can be located below the accommodating plate by the moving mechanism.

6. The device for producing a three-dimensional structural cell according to claim 1, wherein the controller is configured to determine whether or not the cell mass has an appropriate shape on the basis of an image of the cell mass in the accommodating recess portion photographed by the cell mass camera so that the cell mass having an appropriate shape is adsorbed and held by the suction nozzle and the cell mass having an inappropriate shape is not adsorbed and held by the suction nozzle.

* * * * *